US008692678B2

(12) United States Patent
Warner et al.

(10) Patent No.: US 8,692,678 B2
(45) Date of Patent: Apr. 8, 2014

(54) AUTOMATED INTRAVENOUS MONITORING DEVICE

(76) Inventors: Tod. H. Warner, London (CA); Wayne Carman, Toronto (CA)

( * ) Notice: Subject to any disclaimer, the term of this patent is extended or adjusted under 35 U.S.C. 154(b) by 266 days.

(21) Appl. No.: 12/794,042

(22) Filed: Jun. 4, 2010

(65) Prior Publication Data

US 2010/0309005 A1   Dec. 9, 2010

Related U.S. Application Data

(60) Provisional application No. 61/184,023, filed on Jun. 4, 2009.

(51) Int. Cl.
 *G08B 21/00* (2006.01)
(52) U.S. Cl.
 USPC ............. 340/606; 340/603; 340/605; 604/65; 604/67; 604/253
(58) Field of Classification Search
 USPC ............. 340/606, 605, 616, 573.1, 603, 612, 340/618; 604/30, 246, 251, 253, 31, 67, 65
 See application file for complete search history.

(56) References Cited

U.S. PATENT DOCUMENTS

| | | | |
|---|---|---|---|
| 3,563,090 A * | 2/1971 | Deltour | 73/861.41 |
| 3,609,379 A | 9/1971 | Hildebrandt | |
| 4,048,474 A | 9/1977 | Olesen | |
| 4,265,240 A | 5/1981 | Jenkins | |
| 4,346,606 A * | 8/1982 | Cannon et al. | 73/861.41 |
| 4,391,599 A | 7/1983 | Jenkins | |
| 4,396,016 A | 8/1983 | Becker | |
| 4,448,207 A * | 5/1984 | Parrish | 600/584 |
| 4,457,750 A | 7/1984 | Hill | |
| 4,681,569 A * | 7/1987 | Coble et al. | 604/253 |
| 4,898,576 A | 2/1990 | Philip | |
| 5,088,990 A | 2/1992 | Hivale et al. | |
| 5,166,667 A | 11/1992 | Jen | |
| 5,303,585 A * | 4/1994 | Lichte | 73/290 V |
| 5,318,515 A | 6/1994 | Wilk | |
| 5,352,213 A | 10/1994 | Woodard | |
| 5,586,085 A * | 12/1996 | Lichte | 367/99 |
| 5,621,392 A * | 4/1997 | Paolini et al. | 340/603 |
| 6,053,888 A * | 4/2000 | Kong | 604/67 |
| 6,083,206 A | 7/2000 | Molko | |
| 6,099,512 A | 8/2000 | Urrutia | |
| 6,679,865 B2 | 1/2004 | Shekalim | |
| 7,011,651 B2 | 3/2006 | Lee et al. | |
| 7,818,184 B2 * | 10/2010 | Penny et al. | 705/3 |
| 7,918,834 B2 * | 4/2011 | Mernoe et al. | 604/253 |
| 2003/0109836 A1 | 6/2003 | Shekalim | |
| 2004/0068237 A1 | 4/2004 | Bauer | |
| 2004/0171994 A1 | 9/2004 | Goldberg et al. | |
| 2005/0065480 A1 | 3/2005 | Lee et al. | |
| 2006/0020255 A1 | 1/2006 | Cassidy et al. | |
| 2008/0147016 A1 * | 6/2008 | Faries et al. | 604/253 |
| 2009/0314101 A1 * | 12/2009 | Levine | 73/861.08 |

* cited by examiner

*Primary Examiner* — Hung T. Nguyen

(74) *Attorney, Agent, or Firm* — Brett J. Slaney; Blake, Cassels & Graydon LLP

(57) ABSTRACT

An automated intravenous (IV) monitoring device is provided comprising a sensor for sensing drips passing through an IV drip chamber, a processing unit for calculating the total infused volume over a predetermined period of time, and a display for displaying the total infused volume. The IV monitoring device preferably also calculates and displays the flow rate of the drips. Additionally, an alarm can be activated if the flow rate drops below a predetermined value. A method of providing data pertaining to IV drips being infused into a body is also disclosed.

15 Claims, 5 Drawing Sheets

United States Patent US 8,692,678 B2

AUTOMATED INTRAVENOUS MONITORING DEVICE

This application claims priority from U.S. Provisional Application No. 61/184,023 filed on Jun. 4, 2009, the contents of which are incorporated herein by reference.

FIELD OF THE INVENTION

The present invention relates generally to intravenous monitoring devices.

BACKGROUND

When a patient requires the use of an intravenous (IV) drip for the introduction of various fluids into his or her body, it is common for a physician to prescribe a set flow rate in cubic centimeters per hour (cc/hr). A health care provider, usually a nurse, sets this rate manually by turning a small set screw which is located on the IV tubing connected to the patient. The nurse uses his or her best judgment to manually count the number of drips passing through the drip chamber per unit of time and then estimates the drip rate. The nurse must then mentally convert the drip rate measured in drips/minute to a flow rate measured in cc/hr. If the estimated flow is higher or lower than desired, the nurse adjusts the set screw, recounts the drips per unit of time, and re-estimates the flow rate. This process continues until the nurse is satisfied that the prescribed flow rate has been achieved. Naturally, such a process is susceptible to human error. Additionally, it is common for the set flow rate to vary from the prescribed flow rate as the patient moves into different positions. For example, if the patient rolls over and puts pressure on the drip tube, the flow rate may significantly decrease. The nurse will intermittently monitor the flow rate over his or her shift; however, he or she has no way of accurately knowing the total infused fluid over any interval of time apart from the beginning of the shift. Even the latter estimation is subject to error as the intravenous fluid bag is often partially full at the beginning of a shift (i.e., time point zero) and the volume of the intravenous bag at that point in time cannot be measured with precision. If the estimated starting volume is erroneous, then any subsequent estimate of total infused volume will be inaccurate.

Some IV systems include a monitoring device that activates an alarm if the actual drip rate deviates significantly from the prescribed rate. An example of such an alarm is disclosed in U.S. Patent Application Publication No. 2004/0171994 to Goldberg et al. This alarm only causes the nurse to be made aware that the actual drip rate has significantly deviated from the prescribed drip rate. Additionally, the device does not translate the drip rate to a flow rate measured in cc/hr. Once the alarm has been detected, and in order to re-establish the prescribed flow rate, the nurse would have to manually adjust the set screw, count the number of drips per unit of time, estimate the rate, and repeat the process until he or she is satisfied that the flow rate is back to its prescribed value. This process is further complicated in a dark room (e.g. at night) since the nurse would need to use a flashlight to count and monitor the drips, making the entire process more cumbersome and prone to error. It is well-known that the flow rate varies with patient positioning and other patient related factors. It is entirely possible that the flow rate could be at the prescribed rate at the time of the intermittent check by the nurse and be significantly higher or lower at other times. The nurse has no way of knowing of these variances apart from viewing the intravenous fluid bag and estimating the change in volume. As noted, this estimation is subject to measurement error, and is generally not calculated more than once or twice per 8 hour shift. The resultant time lag and/or error in determining a deficiency in intravenous fluid administration could be seriously detrimental to patient care.

It is an object of the present invention to obviate or mitigate at least some of the problems and limitations in administering intravenous fluids.

SUMMARY OF THE INVENTION

In one aspect, an automated IV monitoring device is provided comprising a sensor for sensing drips passing through an IV drip chamber, a processing unit for calculating the total infused volume over a predetermined period of time, and a display for displaying the total infused volume. In some embodiments, the IV monitoring device also calculates and displays the flow rate of the drips. A method of providing data pertaining to IV drips being infused into a body is also provided.

In one embodiment, there is provided an automated IV monitoring device comprising: (i) a sensor for sensing drips passing through an IV drip chamber; (ii) a processing unit for receiving information from the sensor, the information indicating a sensed drip; the processing unit including a memory portion for tracking total infused volume over a predetermined period of time; wherein the processing unit is configured to increment a value in the memory portion upon receiving the information; and (iii) a display in communication with the processing unit, the display configured to indicate the value in the memory portion.

BRIEF DESCRIPTION OF THE DRAWINGS

Exemplary embodiments of the invention will now be described by way of example only with reference to the accompanying drawings, in which.

DETAILED DESCRIPTION OF THE INVENTION

Figure 1:
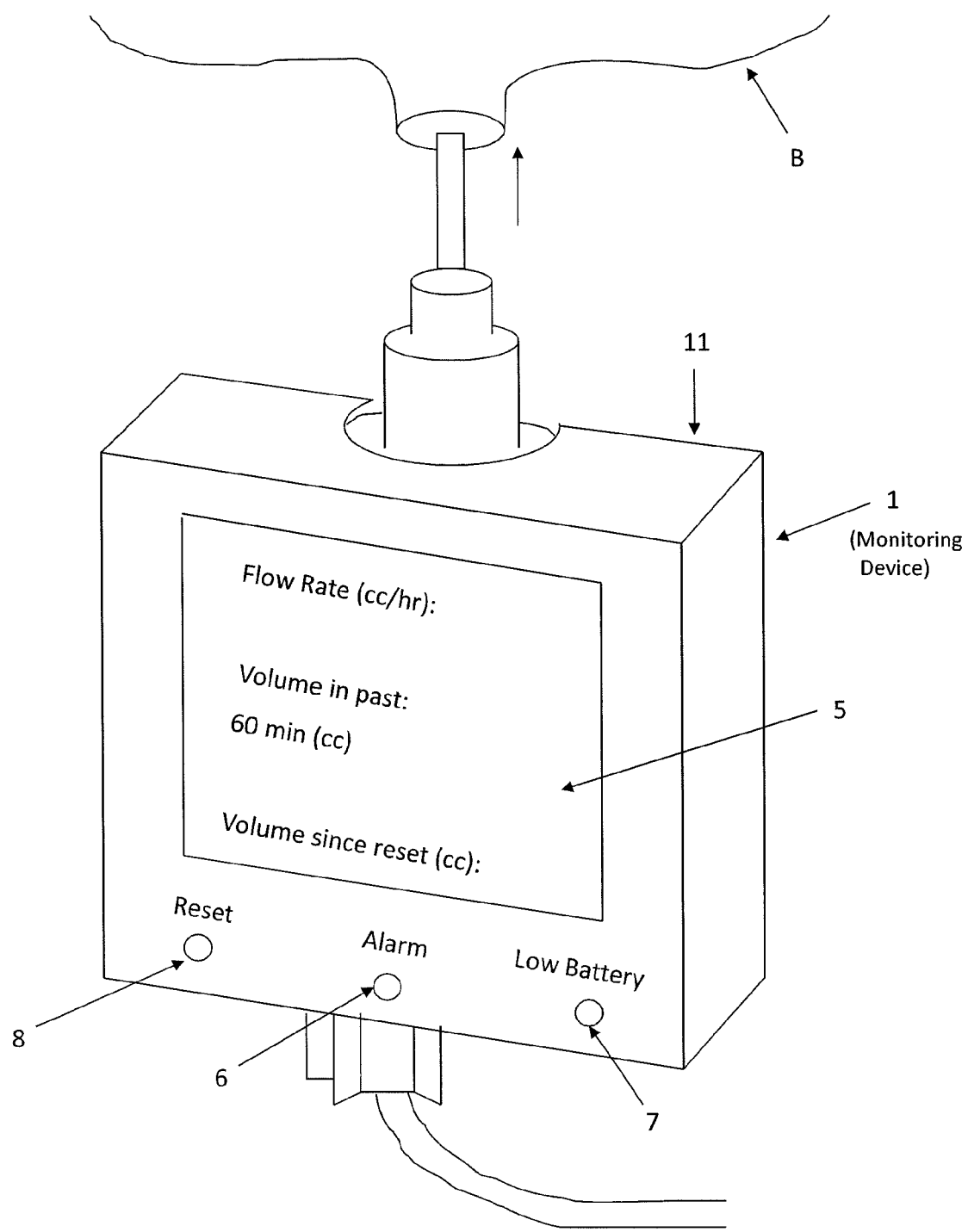
FIG. 1 is a front perspective view an IV monitoring device mounted on a drip chamber.

In general terms, the following provides an automated IV monitoring device that provides real-time monitoring of the actual flow rate, as well as total infused volume from a designated point in time, for example, in the last hour and/or since reset. A display is continually updated to display the flow rate and the infused volume over the predetermined period of time. It has been recognized that by using a processing unit to automatically calculate and display the flow rate and total infused volume in real-time, the nurse can quickly and easily monitor and adjust the flow rate appropriately. The nurse does not have to manually count the drops and estimate the flow rate, rather he or she can simply adjust the set screw and watch the display until the desired flow rate is achieved. For example, in one embodiment, the IV monitoring unit is configured to display the fluid infused in the past hour, as well as since reset (which typically corresponds to the beginning of the nurse's shift). In this embodiment, if a nurse has been absent from the room, upon return, the nurse can immediately read the volume of fluid infused in the past hour and the total fluid infused since the beginning of the nurse's shift. The volume infused in the preceding hour is indicative of any significant changes in the flow rate during the nurse's absence. If the volume infused in the preceding hour is lower than that prescribed, the nurse can appropriately adjust the flow rate to compensate for the patient's deficiency of infused fluid. In other words, the flow rate can be observed to be at an ideal rate at various points in time, but might deviate from the ideal during the intervals between observations. The display of fluid volume infused over the preceding hour allows the nurse to confirm that the flow rate has remained constant. For example, if the flow rate is set at 100 cc/hour and is observed to be 100 cc/hour intermittently, but the fluid volume infused over the past hour is displayed as (say) 65 cc, then the nurse will easily conclude that the intravenous flow was reduced at some point during the last hour because the fluid administered is less than that predicted by the flow rate. The nurse may then take remedial action to compensate for the deficiency of fluid administered and increase the flow rate until the deficiency is corrected. This provides a substantial advantage over previous methods, which rely upon visual inspection of the IV bag volume and manual drip counting. In such previous methods, the recognition of flow discrepancies on an hourly basis is virtually impossible. Patient care may therefore be compromised.

In a representative embodiment, the IV monitor is a small, battery-operated, self-contained unit that easily clips onto a drip chamber. It is compact, portable and easily movable from one IV drip chamber to another. Mounted on the unit is a sensor in close proximity to the IV drip chamber. A variety of sensors can be used; however, the preferred sensor would have no contact with the fluid stream and would not alter the rate of flow.

The sensor detects each drip as it passes through the chamber. A processing unit such as a computer, microprocessor, or microcontroller receives input from the sensor and tracks the time between drips, which is used to calculate the number of drips per hour. Preferably, the processing unit is a small dedicated processing device such as a microcontroller. The flow rate in cc/hr is then calculated and displayed. Additionally, the total infused volume in the last 60 minutes and since reset is calculated and displayed in cubic centimeters (cc). The calculations are repeated continually and the display is updated accordingly to ensure real-time monitoring and display. The unit also includes an alarm that is activated if the flow rate drops below a predetermined value, a reset button, and an indicator that indicates when the battery needs to be replaced.

The unit may be pre-programmed during manufacture to work with a conventional IV drip chamber diameter and drip volume. Optionally, the unit may include a user-interface that allows the user to customize these values. It is contemplated that the user-interface could also allow the customization of many other features, for example: displaying the flow rate in a unit different from cc/hr; turning on or off the alarm; indicating whether the alarm should be audible and/or visual; and allowing the display of total infused volume in time intervals other than the last 60 minutes. These are a sample of the customizable features that may be included. Of course, such features typically come at the expense of increased size of the physical unit and increased power consumption, and therefore may or may not suitable depending on the application.

Figure 2:
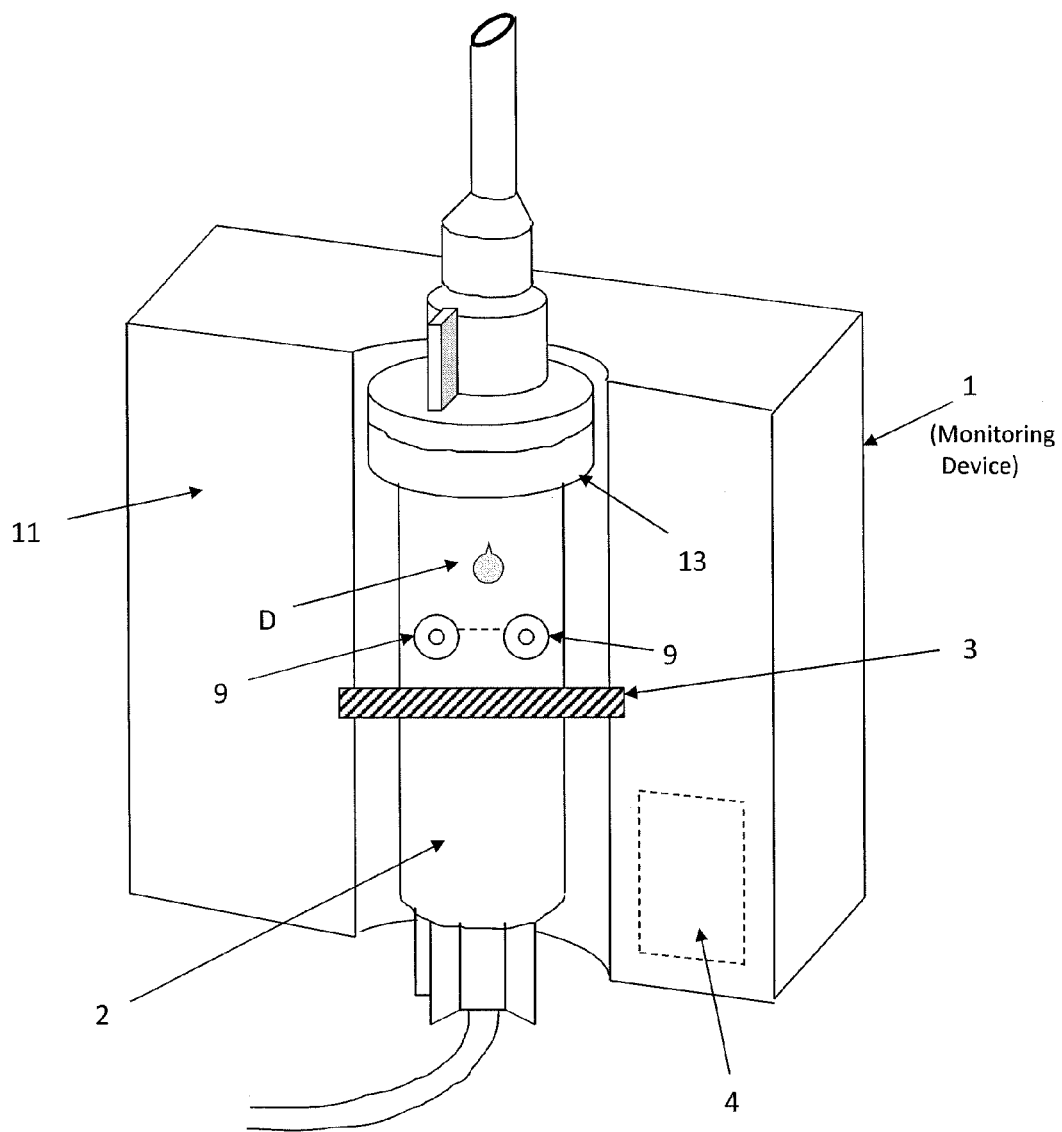
FIG. 2 is a rear perspective view of the IV monitoring device mounted on the drip chamber.
Figure 3:
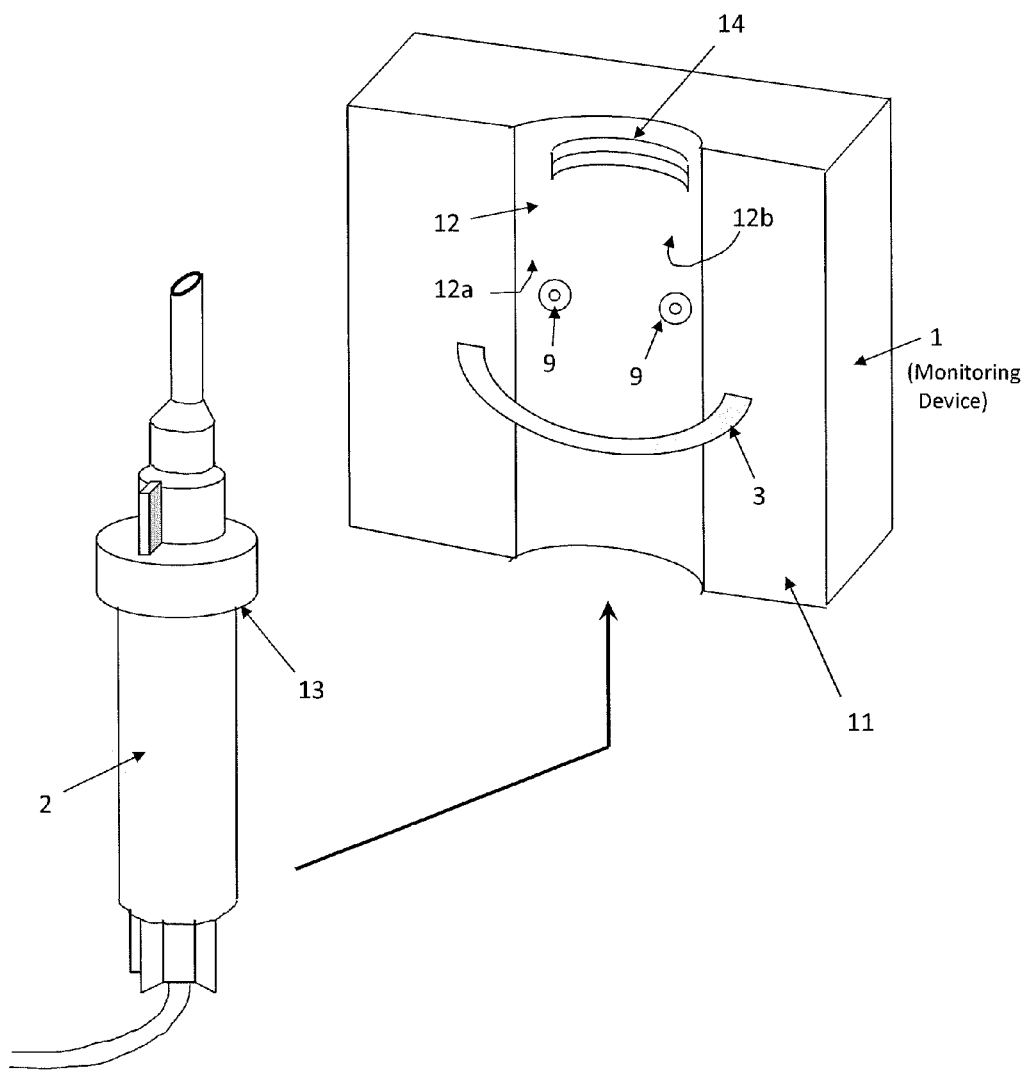
FIG. 3 is a rear perspective view showing the IV monitoring device separated from the drip chamber.

Referring now to FIGS. 1 through 3, an IV monitoring device 1 is shown mounted onto an IV drip chamber 2 using an attachment device such as a strap or mounting clip 3. The drip chamber 2 is connected to an IV drip bag B. The rate at which drips D leave the bag B and pass through drip chamber 2 is controlled by a standard drip rate control mechanism, for example, a set screw (not shown). To increase the flow rate, the set screw is turned to open a valve thereby allowing more liquid drips D through.

All components of the monitoring device 1 are preferably arranged such that the device 1 is compact, portable, and self-contained. As is best shown in FIG. 3, the back 11 of monitoring device 1 includes a cylindrical groove 12 for receiving the drip chamber 2. When the drip chamber 2 is placed in the cylindrical groove 12, the inside walls 12a and 12b of the groove 12 partially wrap around the drip chamber 2. A drip chamber 2 typically has a flange or projecting collar 13 near the top of the drip chamber 2 as part of the connecting member for connection to the drip bag B. Therefore, the cylindrical groove 12 of the monitoring device 1 further includes a circumferential indent 14 for receiving the projecting collar 13. This allows the drip chamber 2 to be received more snugly within the cylindrical groove 12.

A sensor 9 is located on the walls 12a and 12b of the cylindrical groove 12 in close proximity to the drip chamber 2. The walls 12a and 12b form a housing for accommodating the sensor 9. Advantageously, in one embodiment, the sensor 9 comprises a light emitting diode (LED) on one side wall 12a of cylindrical groove 12, and located directly in front of the LED on the opposite side wall 12b of the cylindrical groove 12 is a recover.

The monitoring device 1 is preferably powered by a battery 4. As is shown in FIG. 1, the monitoring device includes a bright display 5 that displays the following parameters in real-time: (a) the flow rate in cubic centimeters per hour (cc/hr); (b) the running-total of the volume of liquid infused in the last 60 minutes in cubic centimeters (cc); and (c) the running-total of the volume of liquid infused since reset in cc. The monitoring device 1 also includes an "Alarm" LED 6 that lights up when an alarm is activated and a "Low Battery" LED 7 that lights up when the battery 4 needs to be replaced. The monitoring device 1 can be reset by the user by activating Reset button 8 or a reset mechanism providing similar functionality. The monitoring device 1 also includes a sensor 9 that is in close proximity to the drip chamber 2.

Figure 4:
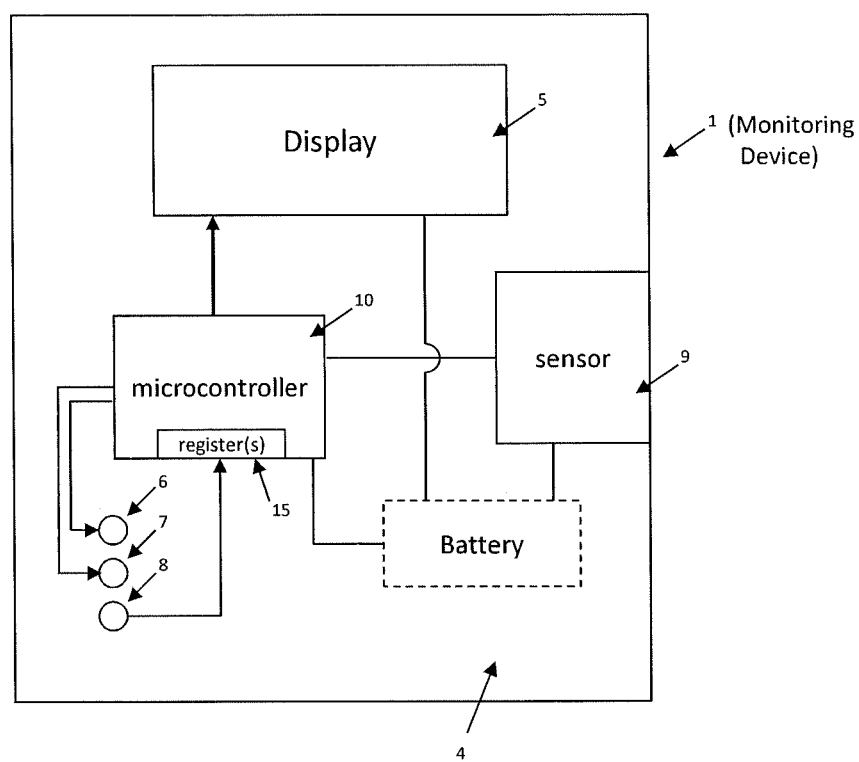
FIG. 4 is schematic view of the internal circuitry of the IV monitoring device.

Referring additionally now to FIG. 4, a processing unit, such as a microprocessor or microcontroller 10, receives input from the sensor 9, as well as the Reset button 8. The microcontroller 10 calculates the flow rate and total volume and updates the display 5. The microcontroller 10 also updates the Alarm LED 6 and Low Battery LED 7 as needed.

One or more memory portions, such as random access memory, counters, or (as shown in the illustrated embodiment) registers 15, are included in the microcontroller 10 for tracking the total infused volume. These registers 15 are reset to zero either by the Reset button 8 or (in the case of tracking the total infused volume each hour) by a counter or equivalent clock-driven functional block (not shown) that keeps track of the duration of each hour.

In operation, the sensor 9 detects drips D passing through the IV chamber 2 and indicates the presence of a drip D to the microcontroller 10. The microcontroller 10 has a timer or clock that calculates the time between drips D and uses this information to calculate the average number of drips per hour. The flow rate in cc/hr is calculated by multiplying the average number of drips per hour by the volume (in cc) of each drip D passing through the chamber. In the preferred embodiment, the average volume of a drip D is stored in memory in the microcontroller 10 and is used in the flow rate calculation. Therefore, the sensor 9 only detects that a drip D has occurred, not the volume of each drip. The average volume of each drip D may be programmed into the microcontroller 10 during manufacture, or it may be customized or calibrated by the user via a user-interface (not shown) or through a data port or other connection. Alternatively, a more advanced sensing device may instead be used that functions to detect the volume of each drip D passing through the chamber and to send this information to the microcontroller 10.

The presence of each detected drip D, as well as its volume, is also used by the microcontroller 10 to keep a running-total of the infused volume in the last 60 minutes and the infused volume since the Reset button 8 was pressed. In operation, the sensor 9 senses a drip D passing through the drip chamber 2 and forwards this information to the microcontroller 10. The microcontroller 10 increments the one or more registers 15 upon receiving this information. The value(s) in the one or more registers 15 are forwarded to the display 5 on a continual basis to thereby provide real-time monitoring of the total infused volume over the designated period of time (e.g. from reset and within the last 60 minutes).

As described above, in the illustrated embodiment, once the flow rate and two new total infused volumes are calculated, the microcontroller 10 updates the display 5 accordingly. The calculations are repeated after the detection of each subsequent drip D, and the display 5 is updated on a continual basis. The repeated calculations and continual updating of the display provide real-time monitoring and display of the flow rate and total infused volume, thereby allowing for simple and error-free calculation and monitoring of these values by a nurse. The nurse can simply observe and modify the IV flow rate by watching the display 5. Additionally, if the flow rate drops below a predetermined value, the microcontroller 10 will activate an alarm, for example, by lighting the Alarm LED 6. The predetermined value that triggers alarm activation may be programmed into the microcontroller 10 during manufacture, or in other embodiments it may be set by a user via a user-interface (not shown).

The embodiment described above is particularly advantageous when a team of nurses is monitoring and adjusting the flow rate and infused volume over the course of many hours or days. Initially, when the physician prescribes a flow rate, the on-shift nurse can simply adjust the set screw and watch the display 5 until the prescribed flow rate is achieved. There is no need to manually count the drips D and estimate the flow rate. The nurse can then leave the patient and check back periodically. In the situation that a patient moves into a position that causes the flow rate to be temporarily disrupted, upon return the nurse will immediately see the displayed total infused volume and recognize that it is lower than the prescribed target, therefore indicating that the flow rate had been disrupted in his or her absence. The nurse can then easily increase the flow rate to compensate for the lack of infused volume. If the patient rolls onto part of the drip tube or moves in any way that significantly hinders the flow rate, the microcontroller 10 will activate the alarm 6. In reacting to the alarm 6, the nurse can simply adjust the flow rate back to the prescribed value by moving the set screw and watching the display 5. There is no need to manually count the drips D and estimate the flow rate. Also, the nurse can use the total infused volume to easily determine the amount of infused volume disrupted during the alarm and compensate accordingly. This reduces or even eliminates human error by using a bright, easy to read display, and simplifies the process even in a dark room at night. In this way, the nurse does not need to turn on a light or use a flashlight to view the IV drip bag or adjust the IV drip rate with accuracy, thus minimizing patient disruptions. The display 5 can also be illuminated either automatically, selectively, or otherwise to facilitate the process of capturing the data.

Additionally, a nurse would want to ensure the correct volume has been infused over the course of his or her shift. The Reset button 8 allows a new nurse at the beginning of his or her shift to press the button 8 and begin tracking the total infused volume from that point. The "Low Battery" LED 7 indicates to any nurse checking on the patient that the battery needs to be replaced. Other set points could also be recorded by programming the microcontroller 10 such that a total infused volume since that set point was recorded is displayed or can be referred to at a later time.

It will be appreciated that various features of the monitoring device 1 may be added or substituted. For example, an alternative embodiment could include a user-interface that allows partial or complete customization of the display and alarm features. The sensor 9 may comprise a visible LED and recover, or could operate on other principles. It is preferred, though, that the sensor 9 have no contact with the fluid stream, thereby allowing the device 1 to be easily portable.

Figure 5:
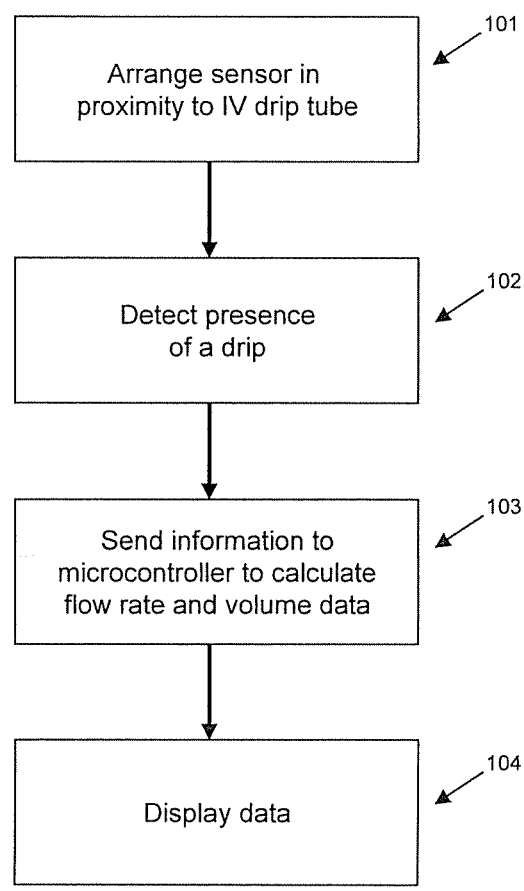
FIG. 5 is a schematic of a set of computer executable instructions for providing data pertaining to IV drips being infused into a body.

Turning now to FIG. 5, there is shown a set of computer readable instructions stored on a computer readable medium, the computer readable instructions for providing data, such as flow rate and/or total infused volume data, pertaining to IV drips being infused into a body.

At step 101, a sensor 9 is arranged in proximity to the IV drip chamber 2. The sensor 9 detects the presence of a drip D at step 102. At step 103, the sensor 9 sends this information to the microcontroller 10, which calculates the flow rate and updates the running-total of the volume as described above. The microcontroller 10 updates the display in step 104 to indicate the updated flow rate and total infused volume data. Additional steps (not shown) may include: the microcontroller 10 activating an alarm 6 if the flow rate is below a predetermined value, the microcontroller 10 monitoring the battery life and indicating to the user that the battery needs to be replaced, the user resetting the running-total of the volume using a Reset Button 8, or the user customizing display and alarm features via a user-interface. An apparatus such as that shown in FIGS. 1 to 3, or alternative devices having the same functionality, could perform such a method.

It will be appreciated that any module or component exemplified herein that executes instructions may include or otherwise have access to non-transitory computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the monitoring device 1, microcontroller 10, etc., or accessible or connectable thereto. Any application or module herein described may be implemented using computer readable/executable instructions that may be stored or otherwise held by such computer readable media.

Although the above principles have been described with reference to certain specific embodiments, various modifications thereof will be apparent to those skilled in the art without departing from the spirit and scope of the invention as outlined in the claims appended hereto.

The invention claimed is:

1. An automated intravenous (IV) monitoring device comprising:
 a sensor for sensing drips passing through an IV drip chamber and for outputting information indicative of the drips;
 a processing unit for receiving the information from the sensor, the processing unit being configured to:
  track a total infused volume over a predetermined period of time by incrementing a value in a memory according to the information, the predetermined period of time being adjustable to differ from an interval of time between observations of the monitoring device; and
  calculate an instantaneous flow rate using the information;
 a display in communication with the processing unit, the display configured to display the total infused volume over the predetermined period of time and the instantaneous flow rate separately to enable the total infused volume over the predetermined period of time to reflect variations in the instantaneous flow rate between the observations of the monitoring device; and
 a cylindrical groove for receiving the drip chamber, the cylindrical groove comprising a circumferential indent for receiving a collar on the drip chamber to secure the drip chamber within the cylindrical groove.

2. The IV monitoring device of claim 1 further comprising an alarm configured to activate if the instantaneous flow rate is below a predetermined value.

3. The IV monitoring device of claim 2 wherein the alarm comprises a light emitting diode.

4. The IV monitoring device of claim 1 further comprising a reset mechanism, wherein the value in the memory is reset by activation of the mechanism.

5. The IV monitoring device of claim 1 wherein the monitoring device is removably mountable on the drip chamber.

6. The IV monitoring device of claim 1 wherein the sensor is located on an inside wall of the cylindrical groove to be in close proximity with the drip chamber when the drip chamber is received in the groove.

7. The IV monitoring device of claim 1 wherein the monitoring device is battery-operated and includes a "low battery" indicator.

8. A method of providing data pertaining to IV drips being infused into a body, the method comprising the steps of:
 a sensor of a monitoring device detecting the presence of a drip from an IV drip chamber;
 the sensor forwarding information to a processing unit, the information being indicative of the drip;
 the processing unit tracking a total infused volume over a predetermined period of time by incrementing a value in a memory according to the information, the predetermined period of time being adjustable to differ from an interval of time between observations of the monitoring device;
 the processing unit calculating an instantaneous flow rate using the information; and
 displaying the total infused volume over the predetermined period of time and the instantaneous flow rate separately on a display to enable the total infused volume over the predetermined period of time to reflect variations in the instantaneous flow rate between the observations of the monitoring device;
 wherein the monitoring device comprises a cylindrical groove for receiving the drip chamber, the cylindrical groove comprising a circumferential indent for receiving a collar on the drip chamber to secure the drip chamber within the cylindrical groove.

9. The method of claim 8 further comprising the step of activating an alarm if the instantaneous flow rate is below a predetermined value.

10. The method of claim 8 wherein the value in the memory is resetable using a reset mechanism.

11. The method of claim 8 wherein the monitoring device is battery-operated, and further comprising the step of indicating on the display when the battery needs to be replaced.

12. A non-transitory computer readable medium having stored thereon computer readable instructions for performing a method of providing data pertaining to IV drips being infused into a body, the computer readable instructions including instructions to perform steps comprising:
 a sensor of a monitoring device detecting the presence of a drip from an IV drip chamber;
 the sensor forwarding information to a processing unit, the information being indicative of the drip;
 the processing unit tracking a total infused volume over a predetermined period of time by incrementing a value in a memory according to the information, the predetermined period of time being adjustable to differ from an interval of time between observations of the monitoring device;
 the processing unit calculating an instantaneous flow rate using the information; and
 displaying the total infused volume over the predetermined period of time and the instantaneous flow rate separately on a display to enable the total infused volume over the predetermined period of time to reflect variations in the instantaneous flow rate between the observations of the monitoring device;
 wherein the monitoring device comprises a cylindrical groove for receiving the drip chamber, the cylindrical groove comprising a circumferential indent for receiving a collar on the drip chamber to secure the drip chamber within the cylindrical groove.

13. The non-transitory computer readable medium of claim 12 wherein said instructions further include instructions to perform the step of activating an alarm if the instantaneous flow rate is below a predetermined value.

14. The non-transitory computer readable medium of claim 12 wherein the value in the memory is resetable using a reset mechanism.

15. The non-transitory computer readable medium of claim 12 wherein the monitoring device is battery-operated, and wherein said instructions further include instructions to perform the step of indicating on the display when the battery needs to be replaced.

* * * * *